(12) United States Patent
Tiemann et al.

(10) Patent No.: US 10,551,306 B1
(45) Date of Patent: Feb. 4, 2020

(54) TOMOGRAPHIC APPROACH TO 3-D HOLOGRAPHIC REFRACTOMETRY

(71) Applicant: LOCKHEED MARTIN COHERENT TECHNOLOGIES, INC., Louisville, CO (US)

(72) Inventors: Bruce G. Tiemann, Longmont, CO (US); Brian Krause, Erie, CO (US)

(73) Assignee: Lockheed Martin Coherent, Louisville, CO (US)

(*) Notice: Subject to any disclaimer, the term of this patent is extended or adjusted under 35 U.S.C. 154(b) by 99 days.

(21) Appl. No.: 15/708,068

(22) Filed: Sep. 18, 2017

Related U.S. Application Data

(60) Provisional application No. 62/404,709, filed on Oct. 5, 2016.

(51) Int. Cl.
*G01N 21/45* (2006.01)
*G01N 21/41* (2006.01)

(52) U.S. Cl.
CPC ....... *G01N 21/453* (2013.01); *G01N 21/4133* (2013.01)

(58) Field of Classification Search
CPC .. G01N 21/4133; G01N 21/45; G01N 21/453; G01N 2021/451; G01N 2223/401; G01N 23/06; G01N 23/083
See application file for complete search history.

(56) References Cited

U.S. PATENT DOCUMENTS

| | | | |
|---|---|---|---|
| 2013/0057869 A1* | 3/2013 | Cotte | G02B 21/365 356/457 |
| 2014/0347672 A1* | 11/2014 | Pavillon | A61B 5/0066 356/491 |

OTHER PUBLICATIONS

Charriere, Florian et al. "Cell refractive index tomography by digital holographic microscopy". Optics Letters, vol. 31, No. 2, Jan. 15, 2006, pp. 178-180. (Year: 2006).*
Pavillon, Nicolas et al. "Optical Tomography by Digital Holographic Microscopy". Novel Optical Instrumentation for Biomedical Applications IV, Proc. of SPIE-OSA Biomedical Optics, SPIE vol. 7371, 737104, 2009, pp. 737104-1-737104-6. (Year: 2009).*
Marquet, P. et al. "Red blood cell structure and dynamics explored with digital holographic microscopy". Imaging, Manipulation, and Analysis of Biomolecules, Cells, and Tissues VII, Proc. of SPIE vol. 7182, 71821A, 2009, pp. 71821A-1-71821A-6. (Year: 2009).*

* cited by examiner

*Primary Examiner* — Michael A Lyons
(74) *Attorney, Agent, or Firm* — Morgan, Lewis & Bockius LLP

(57) ABSTRACT

A system for performing 3-dimensional (3-D) digital holographic refractometry includes a splitter to split a source light into a first light beam and a second light beam. A tomographic optical setup shines a sample with the first light beam and generates an image light beam. A detector array generates an interferogram signal in response to being simultaneously exposed to the image light beam and the second light beam.

19 Claims, 9 Drawing Sheets

TOMOGRAPHIC APPROACH TO 3-D HOLOGRAPHIC REFRACTOMETRY

CROSS-REFERENCE TO RELATED APPLICATIONS

This application claims the benefit of priority under 35 U.S.C. § 119 from U.S. Provisional Patent Application 62/404,709 filed Oct. 5, 2016, which is incorporated herein by reference in its entirety.

STATEMENT REGARDING FEDERALLY SPONSORED RESEARCH OR DEVELOPMENT

Not applicable

FIELD OF THE INVENTION

The present invention generally relates to refractometry, and more particularly, to an improved tomographic approach to 3-D holographic refractometry.

BACKGROUND

As the development of material with variable refractive index progresses, measuring the refractive index of a sample in 3-D becomes more desirable. For some optical samples, the refractive index does not remain constant throughout the thickness of the sample. For example, a gradient index (GRIN) lens may be made from materials with refractive indexes that vary throughout the thickness of the lens. Additionally, there are active programs to develop a material with writable index. A sample material with writable index can be made, for instance, by selectively exposing locations of the sample to laser light, and then heat-treating the entire sample. Exposing to laser light causes deposition of nanocrystals of a higher-index phase in the exposed locations. The initially formed nanocrystals may be annealed into larger grains of overall higher refractive index than the unexposed material. Lengthier exposure times lead to greater refractive index changes (increases).

Using focusing optics, regions of the sample can be exposed in close proximity to other regions that remain unexposed, allowing the possibility of writing what can later become index features in the finished sample. The process is nonlinear, enabling light that is projected into a focus to expose a region at a certain depth in the material (e.g., at the high-intensity focus of the light), while leaving material both at lesser and at greater depths relatively unexposed. This results in producing an isolated high refractive index island in 3-D, a process that can be replicated throughout the volume of the sample. Thus, leveraging this method, it is possible to write refractive-index features in full 3-D.

SUMMARY

According to various aspects of the subject technology, methods and configuration are disclosed for application of tomographic methods to 3-D digital holographic refractometry. In some aspects, the subject technology provides an improved method of determining the actual 3-D index of the material, such that to allow the process of writing refractive-index features to ultimately generate the desired index profile as accurately as possible.

In one or more aspects, a system for performing 3-dimensional (3-D) digital holographic refractometry includes a splitter to split a source light into a first light beam and a second light beam. A tomographic optical setup shines a sample with the first light beam and generates an image light beam. A detector array generates an interferogram signal in response to being simultaneously exposed to the image light beam and the second light beam.

In other aspects, a method for performing 3-D digital holographic refractometry includes splitting a source light into a first light beam and a second light beam. A sample positioned in an angle relative to a reference plane is shined with the first light beam to generate an image light beam. The second light beam is configured to combine with the image light beam to produce a combined light beam at a detection plane parallel to the reference plane. A detector array is used to detect the combined light beam to generate an interferogram frame pertaining to an angular position of the sample.

In yet other aspects, a 3-D digital holographic refractometry system includes a light source, a splitter, an optical setup, a detector array and a processor. The light source generates a light beam. The splitter splits the light beam into a first beam and a second beam. An optical setup is configured to hold a sample in a number of angular positions and to allow the sample to be shined at each angular position with the first beam and to generate a corresponding image light beam for that angular position. The detector array generates interferogram frames in response to being simultaneously exposed to the image light beam and the second beam when the sample is held in various angular positions. The processor is configured to process the interferogram frames to generate a 3-D refractive index of the sample.

The foregoing has outlined rather broadly the features of the present disclosure in order that the detailed description that follows can be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific aspects of the disclosure, wherein.

DETAILED DESCRIPTION

Figure 1:
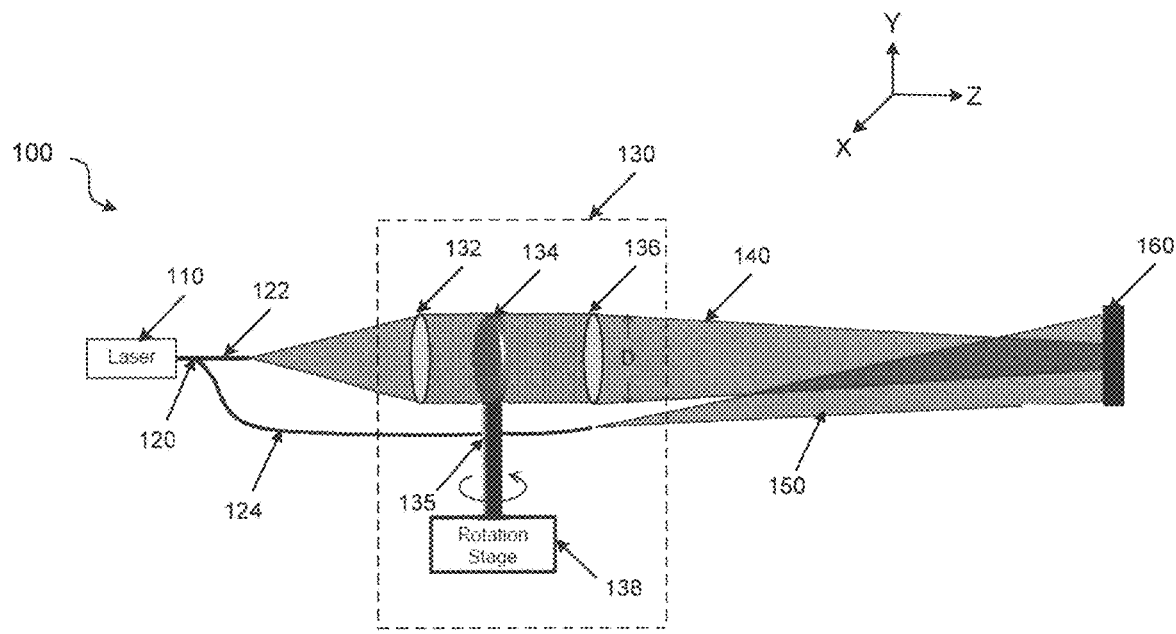
FIG. 1 is a diagram illustrating an example system for performing 3-D digital holographic refractometry, according to certain aspects of the disclosure.

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and can be practiced using one or more implementations. In one or more instances, well-known structures and components are shown in block diagram form in order to avoid obscuring the concepts of the subject technology.

In some aspects of the present technology, methods and configurations are described for using tomographic approaches to perform 3-D digital holographic refractometry. In the process of writing refractive-index features, a multi-element corrector lens assembly is used, which is cumbersome and it is desirable to replace it with a single-element lens. However, doing so requires the single-element lens to have a complex 3-D index profile that is not presently manufacturable with current glass technology. Accordingly, developing materials and processes for 3-D index modification and measurement are of particular interest. Especially, the necessary optical material may have a varying refractive index that varies with both depth and radius from a center of an optical material sample. Such an optical material may be made neither by the usual process of co-melting stacked plates of differing refractive indexes, nor by gradient melting, used to make spherical-aberration-corrected singlet lenses, despite having spherical surfaces.

The disclosed solution is based on the application of tomographic methods to 3-D digital holographic refractometry. The subject approach includes several advantages over the conventional approaches as described herein. Conventional (e.g., non-holographic) imaging interferometers may use either focal plane arrays (FPAs) that are as large as the beam being measured (e.g., a 4 inch FPA to measure a 4 inch optic) or precision optics to reduce the beam to the dimensions of a smaller array. In contrast, the disclosed improved digital holographic methods can manage focused beams and do not require special components by way of condensing optics, for a specific size. An alternative approach is phase shifting interferometry that requires collecting multiple frames and using a pair of acousto-optic modulators (AOMs) to produce a frequency offset between the signal and the local oscillator (LO). The phase shifting interferometry further requires system stability during the multiple frame collection. The disclosed approach captures phase information in a single frame. Although multiple frames can be used to average shot noise, but the frame-to-frame stability requirement is greatly relaxed since it allows incoherent averaging.

Refractive index can be accurately measured using ellipsometry techniques that only work for surfaces, including buried surfaces (e.g., as in multilayer dielectric coatings). The ellipsometry technique, however, may not work for complex 3-D index profiles of interest in the present disclosure. Other approaches include using a pupil plane imaging setup, which requires a plane wave reference and is not as simple as the disclosed approach.

In one or more implementations of the subject technology, the tomographic 3-D digital holographic refractometry begins with capturing an interferogram by the following steps: 1) place a sample on a rotation stage; 2) shine the sample with a coherent light source; 3) focus the transmitted light onto a 2D focal plane array; 4) simultaneously illuminate the 2D focal plane array (e.g., a detector array) with mutually coherent LO light to create the interferogram on the 2D focal plane array; 5) capture the interferogram; and 6) repeat steps 1 through 5 with the sample stepped by a small angle of rotation over the entire locus of desired angles. In some aspects, the steps may be of rotation in one dimension or in two dimensions. For example, in angle-angle space, the sampled angles may be many points along one line, a square grid of points, a rectangular grid of points with different number and/or spacing in the two directions, a locus of rows of points situated at different non-perpendicular angles, and intersecting at the center, or other geometries.

In some aspects, the captured interferogram may be processed by capturing each interferogram into a frame showing an optical phase as a function of position in the sample, and then applying tomographic processing to the stack of frames using a tomographic algorithm. If the writing process changes the refractive index in only one direction (increase or decrease), this can be used as a constraint in an iterative algorithm that computes missing information due to limited angular range. Lens errors can be corrected by taking a frame without the sample present, for example, with the light only going through the lens, instead of the lens and the sample. Processing the frame can give the aberrations of the lens, which can be subtracted from sample frames. Because the correction of lens error in the disclosed solution is easy to implement, the requirements on the lens is not excessive, unlike the majority of interferometric applications which place great demands on the optics used.

FIG. 1 is a diagram illustrating an example system 100 for performing 3-D digital holographic refractometry, according to certain aspects of the disclosure. The system 100 includes a light source (e.g., a laser) 110, a splitter 120, a tomographic optical setup 130 and a detector array 160. The splitter 120 splits the light from the light source 110 into a first beam carried by a waveguide 112 and a second beam carried by a second waveguide 124. The tomographic optical setup 130 includes a first optical lens 132, a second optical lens 136, a sample 134 held by a rotating sample holder 135 that is rotated by a rotation stage 138. The rotation stage 138 enables rotation of the sample 134 with an angular span covering a range of about 0 to 180 degrees. For example, at zero degree, a plane of the sample 134 can be parallel to a reference plane (e.g., X-Y plane). Further, the sample holder 135 allows rotation of the sample 134 along various axes of rotation. In other words, the sample 134 can be tilted away from an initial position including the Y axis and be fixed at a number of tilt angles with respect to the Y axis.

In some aspects, the sample 134 may be a shard of a pyrex stirring rod placed inside a cell filled with oil having a refractive index matched with the refractive index (e.g., about 1.47) of the sample 134. The first light beam from the waveguide 122 shines the sample through the first optical lens 132. An image light beam 140 from the sample is focused, via the second lens 136, on the detector array 160 positioned at a focal plane of the second lens 136. In some aspects, the detector array 160 may be positioned in an intermediate plane between a pupil plane and an imaging plane to avoid saturating the detector array. The detector array 160 can be any light detector array, for example, a charge-coupled device (CCD). The plane of the detector array 160 can be parallel to the reference plane. The detector array 160 is further shined with the second light beam 150 (also referred to as local oscillator (LO) beam) of the waveguide 124. At the detector array 160, the image light beam 140 is combined with the second light beam 150 and generates an interferogram frame pertaining to a current angular position of the sample 134. The sample 134 can be rotated form about 0 to 180 degrees at various tilt angles. This results in a number of corresponding interferogram frames which can be captured into memory and processed by one or more processors. The memory and the processor may be part of an electronic device such as a computing device (e.g., a desktop, a laptop or another computing device) coupled to the detector array 160. The output result of the processing of the interferogram frames is a 3-D refractive index of the sample material of the sample 134. In some implementations, the system 100 may include a writing beam (not shown for simplicity) to enable writing a refractive index onto the sample 134, at each angular position, to achieve a desired 3-D refractive index. The writing beam may have a different wavelength than the first beam and the second beam discussed above.

Figure 2:
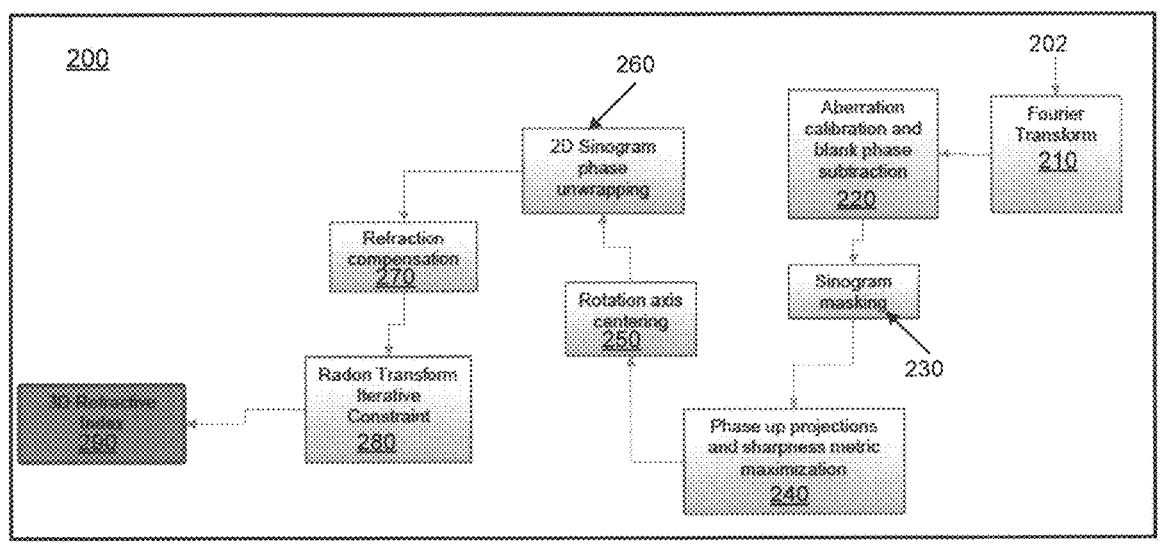
FIG. 2 is a block diagram illustrating an example system for processing interferogram signals, according to certain aspects of the disclosure.

FIG. 2 is a block diagram illustrating an example system 200 for processing interferogram frames 202, according to certain aspects of the disclosure. The system 200 includes a Fourier transform module 210, an aberration calibration and blank phase subtraction module 220, a sinogram masking module 230, a phase-up projections and sharpness metric maximization module 240, a rotation axis centering module 250, a 2-D sinogram phase unwrapping module 260, a refraction compensation module 270 and a radon transform iterative constraint module 280. The system 200 processes the interferogram frames 202 generated by the detector array 160 of FIG. 1 to create a 3-D refractive index 290 of the sample material of the sample 134 of FIG. 1.

The Fourier transform module 210 receives the interferogram frames 202 (e.g., raw hologram data) from the detector array 160 and performs hologram processing including a 2-D Fourier transform processing, for example, fast Fourier transform (FFT) on the received data. The FFT processing generates, for each interferogram frame 202 an intensity data and a phase data in spatial frequency domain. The hologram processing further includes processing of the phase data by the aberration calibration and blank phase subtraction module 220, where a calibration phase data is subtracted from the phase data to generate a phase projection. The calibration phase data can be collected with system 100 of FIG. 1 and with the sample 134 removed. The subtraction of the calibration data can remove artifacts due to lens aberration and system defocus. Further, a background phase (e.g., phase of a sample prior to index changes) is subtracted from the phase projection to produce a final phase projection that can be used by the sinogram masking module 230. Details of the functionalities and results of the processing by the remaining of the above-mentioned processing modules are discussed with respect to the FIGS. 3 through 9 described below.

Figure 3:
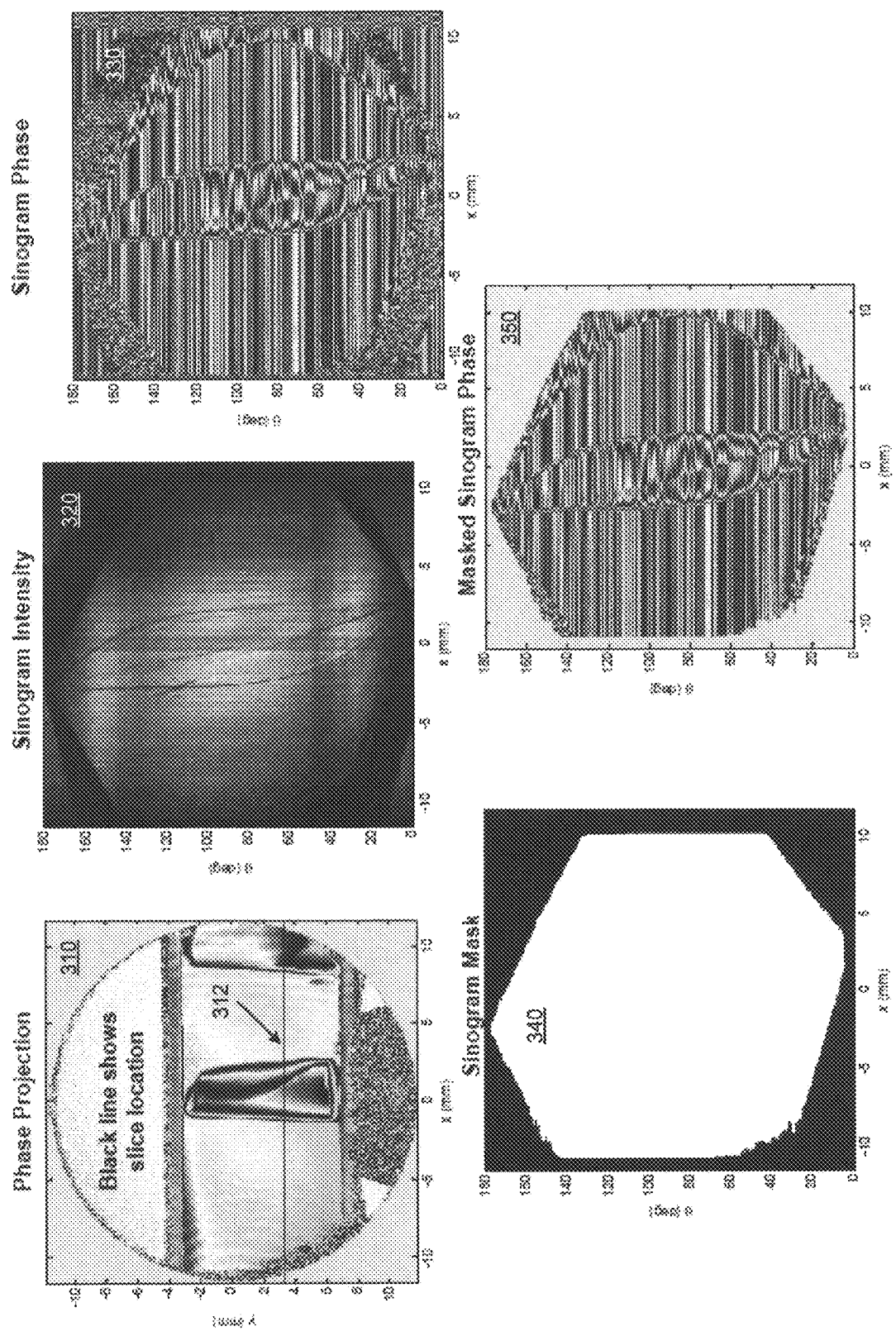
FIG. 3 is a diagram illustrating example intermediate processing results of the system of FIG. 2, according to certain aspects of the disclosure.

FIG. 3 is a diagram illustrating example intermediate processing results of the system of FIG. 2, according to certain aspects of the disclosure. The phase projection 310 generated by the aberration calibration and blank phase subtraction module 220 of FIG. 2 includes phase data corresponding to several elevations. For each elevation, for example, corresponding to a line 312, a sinogram intensity 320 and a sinogram phase 330 are generated. In some aspects, the sinogram masking module 230 of FIG. 2 applies a known sinogram mask 340 to the sinogram phase 330 to generate a masked sinogram phase 350. The masking can improve performance of a following projection phasing up processing step.

Figure 4:
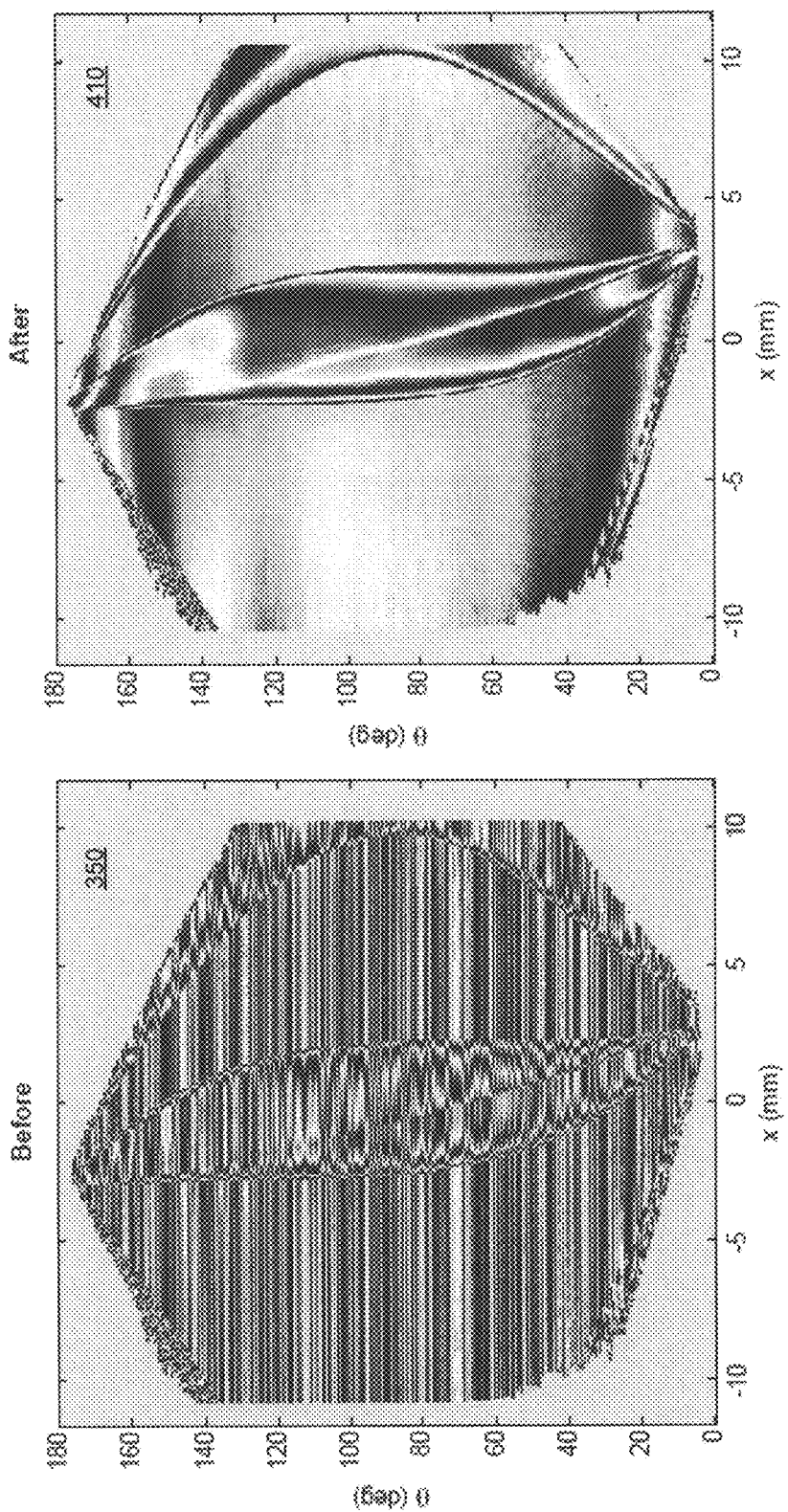
FIG. 4 is a diagram illustrating an example phasing up processing result of the system of FIG. 2, according to certain aspects of the disclosure.

FIG. 4 is a diagram illustrating an example phased-up phase sinogram 410 of the system 200 of FIG. 2, according to certain aspects of the disclosure. It is understood that small movements between frames and/or thermal changes in the optical fibers (e.g., waveguides 122 and 124) may cause phase errors such as the known random piston phase errors. The phase-up projections and sharpness metric maximization module 240 (hereinafter "the module 240") can compute and remove these phase errors from the masked sinogram phase 350 using a maximum likelihood phase gradient estimator, which is a known calculation often used in processing synthetic aperture radar imagery. In some aspects, when there is prior knowledge that the sample has a zero background, the module 240 applies an image sharpness metric maximization algorithm to further improve the phase error removal calculation. The result of the phasing up process is a phased-up phase sinogram 410.

Figure 5C:
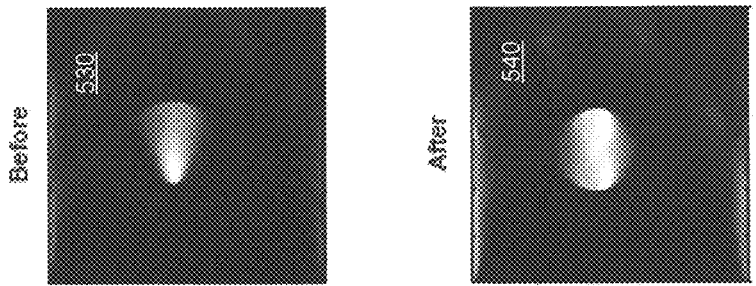
FIGS. 5A through 5C are diagrams illustrating examples of rotation axis centering processing results of the system of FIG. 2, according to certain aspects of the disclosure.
Figure 5B:
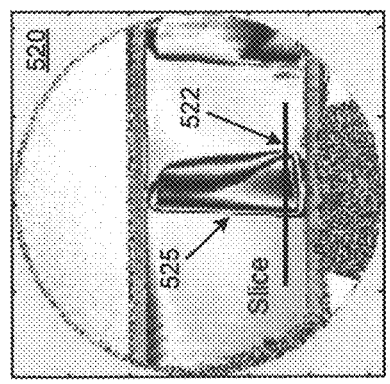
Figure 5A:
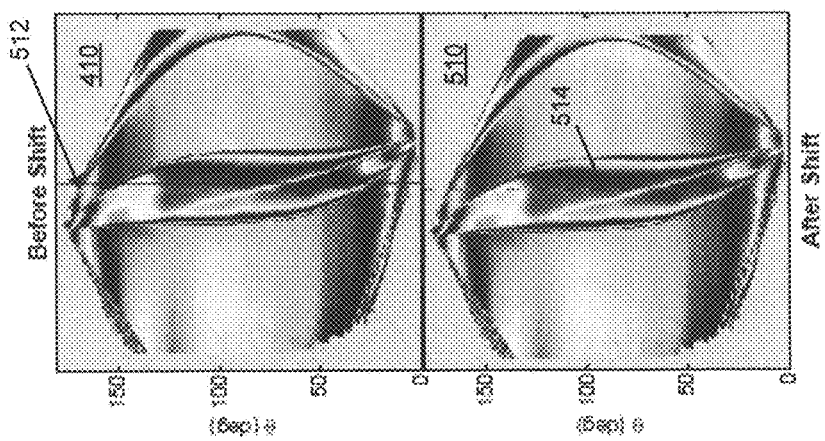

FIGS. 5A through 5C are diagrams illustrating examples of rotation axis centering processing results of the system of FIG. 2, according to certain aspects of the disclosure. Image distortions can result if a horizontal center of the sinogram is not the axis of rotation of the sample. The axis of rotation before shift is shown as a line 512 on the phased-up phase sinogram 410 of FIG. 5A. The axis of rotation after the shift is shown as a line 514 on the phase sinogram 510 of FIG. 5A. A cross section location slice 522, shown on the phase projection 520 of FIG. 5B, is located at a circular part of the sample 525. The rotation axis centering module 250 of FIG. 2 is responsible for centering of the rotation axis line 512. Image 530 of FIG. 5C is before rotation axis centering and shows a distortion, which is removed by the rotation axis centering, as shown in an after rotation axis centering image 540 of FIG. 5C.

Figure 6:
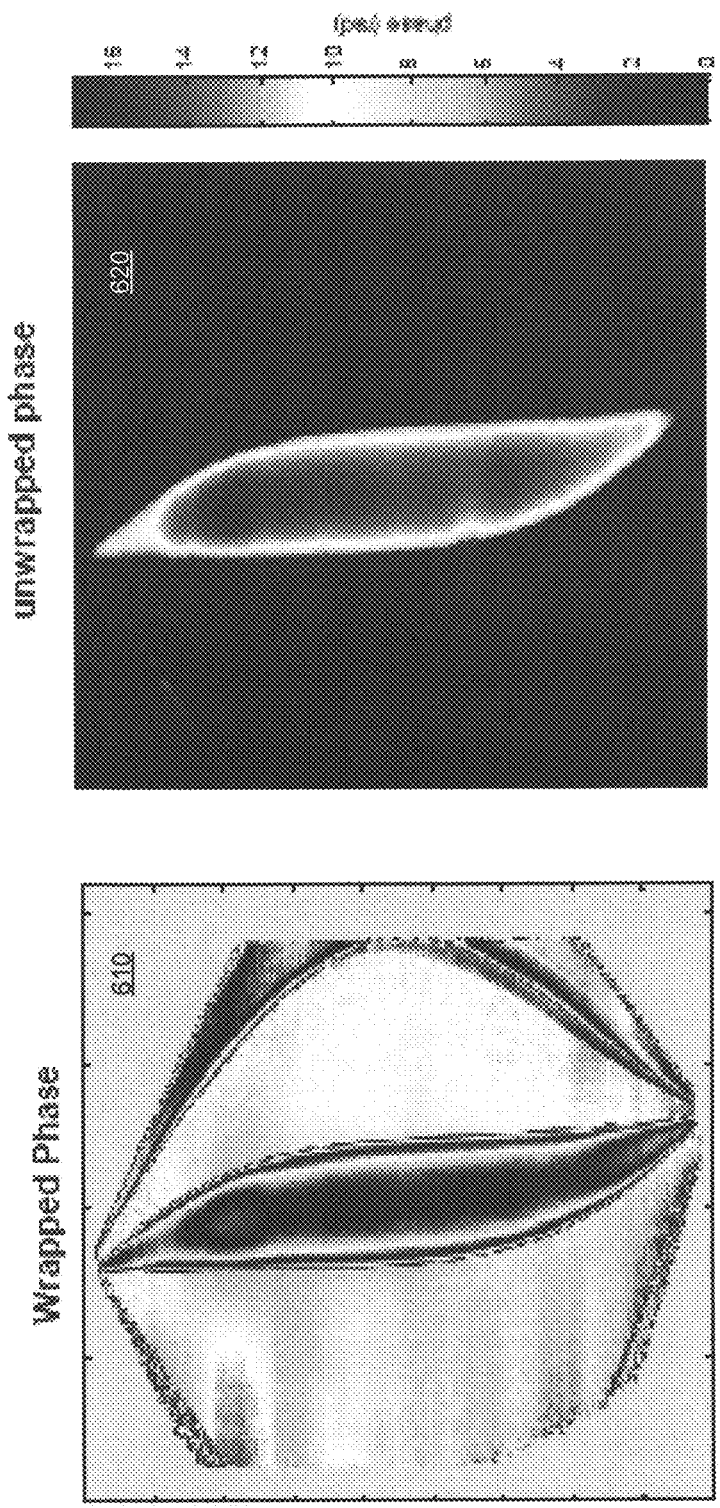
FIG. 6 is a diagram illustrating examples of sinogram unwrapping processing results of the system of FIG. 2, according to certain aspects of the disclosure.

FIG. 6 is a diagram illustrating an example of a sinogram phase unwrapping processing result 610 of the system 200 of FIG. 2, according to certain aspects of the disclosure. The 2-D sinogram phase unwrapping module 260 of FIG. 2 applies one or more known 2-D phase unwrapping algorithm(s) to unwrap the sinogram phase of a wrapped sinogram phase 610 of FIG. 6 to produce the unwrapped sinogram phase result 620. For example, an unweighted least squares phase unwrapping method may be used to process the wrapped phase 610 and generate unwrapped phase 620 of FIG. 6. This may result in distortion and errors, for which techniques for improvement may use a weighted least squares unwrapper to unwrap both the phase projection and the sinogram.

Figure 7:
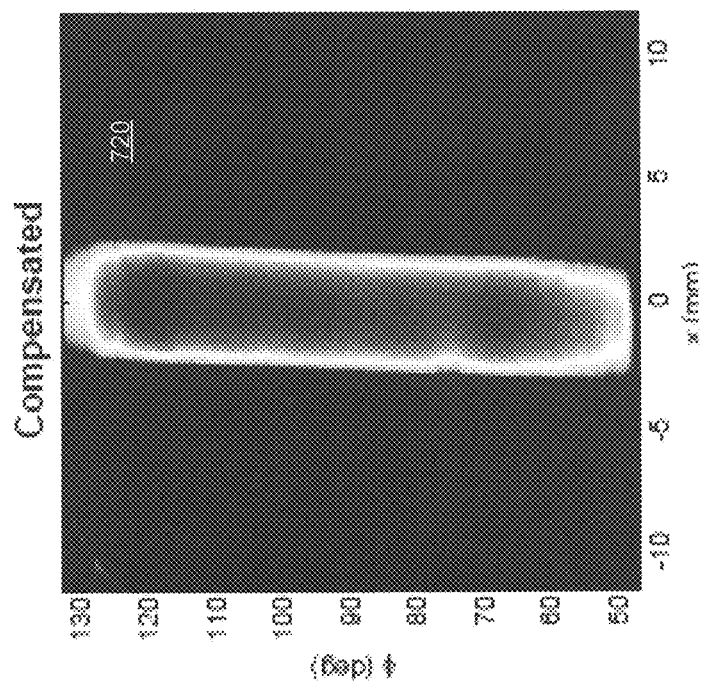
FIG. 7 is a diagram illustrating an example of refraction compensation processing results of the system of FIG. 2, according to certain aspects of the disclosure.
Figure 7:
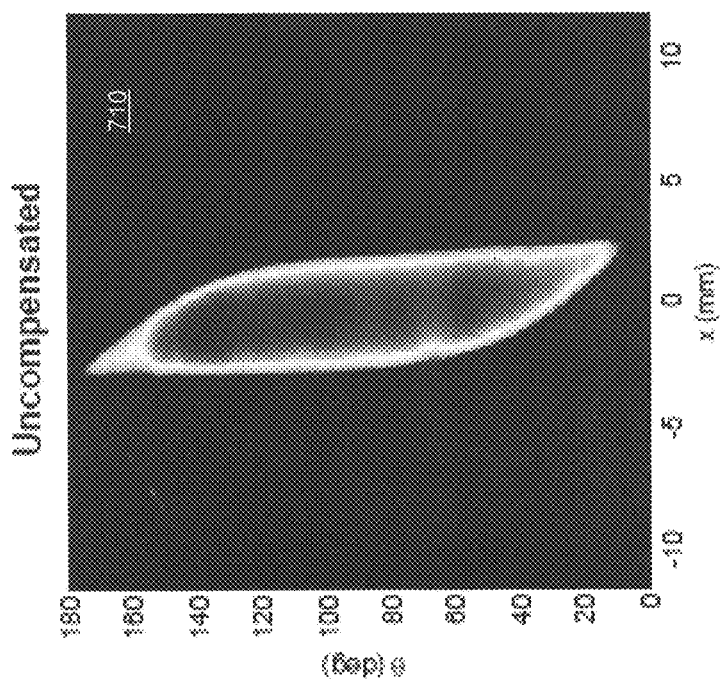

FIG. 7 is a diagram illustrating examples of refraction compensation processing results of the system 200 of FIG. 2, according to certain aspects of the disclosure. The refraction compensation module 270 of FIG. 2 is responsible for compensating the refraction. The refraction compensation module 270 may apply analytic transformations to remove the effect of refraction at the interface of air and the sample at the front and back surfaces of the sample. The sinograms 710 and 720 of FIG. 7 are uncompensated and compensated sinograms, respectively.

Figure 8:
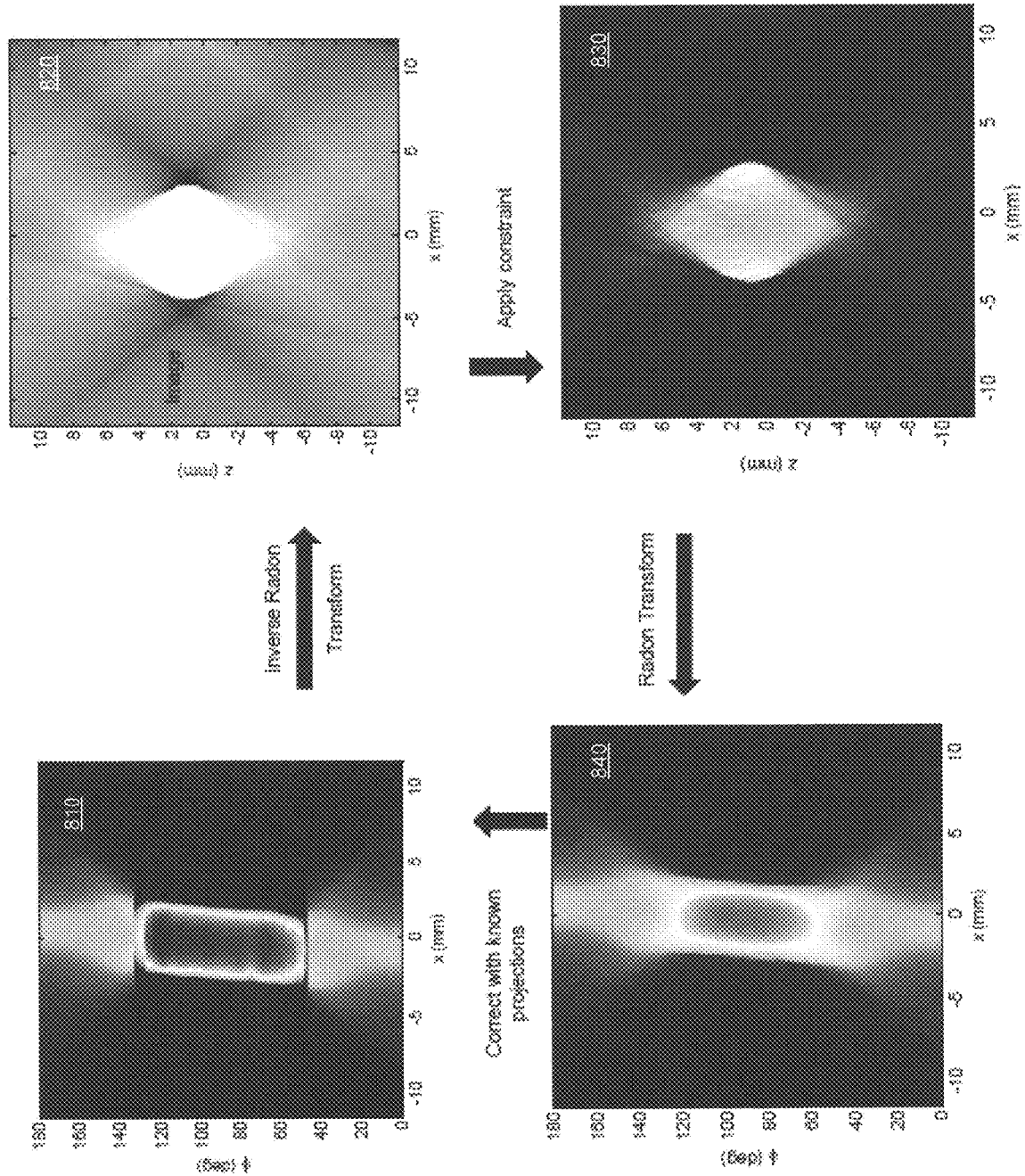
FIG. 8 is a diagram illustrating examples of radon transform processing results of the system of FIG. 2, according to certain aspects of the disclosure.

FIG. 8 is a diagram illustrating examples of radon transform processing results of the system 200 of FIG. 2, according to certain aspects of the disclosure. Due to the higher index of refraction of the sample (e.g., 134 of FIG. 1), steep angles through the sample cannot be observed, which can result in missing projection data. The radon transform iterative constraint module 280 of FIG. 2 (hereinafter "the module 280") can estimate the missing information using a known radon transform iterative constraint algorithm. Starting with a sinogram 810 of FIG. 8, the module 280 computes the corresponding image slice 820 using the inverse radon transform. Then, using the knowledge that the index writing process only makes positive changes in the index of refraction, the module 280 applies a nonnegative constraint to the image to form the image 830. The module 280 then applies a radon transform to compute a corresponding sinogram 840. Finally, the module 280 replaces the part of the sinogram with known projections and repeats the process.

Figure 9:
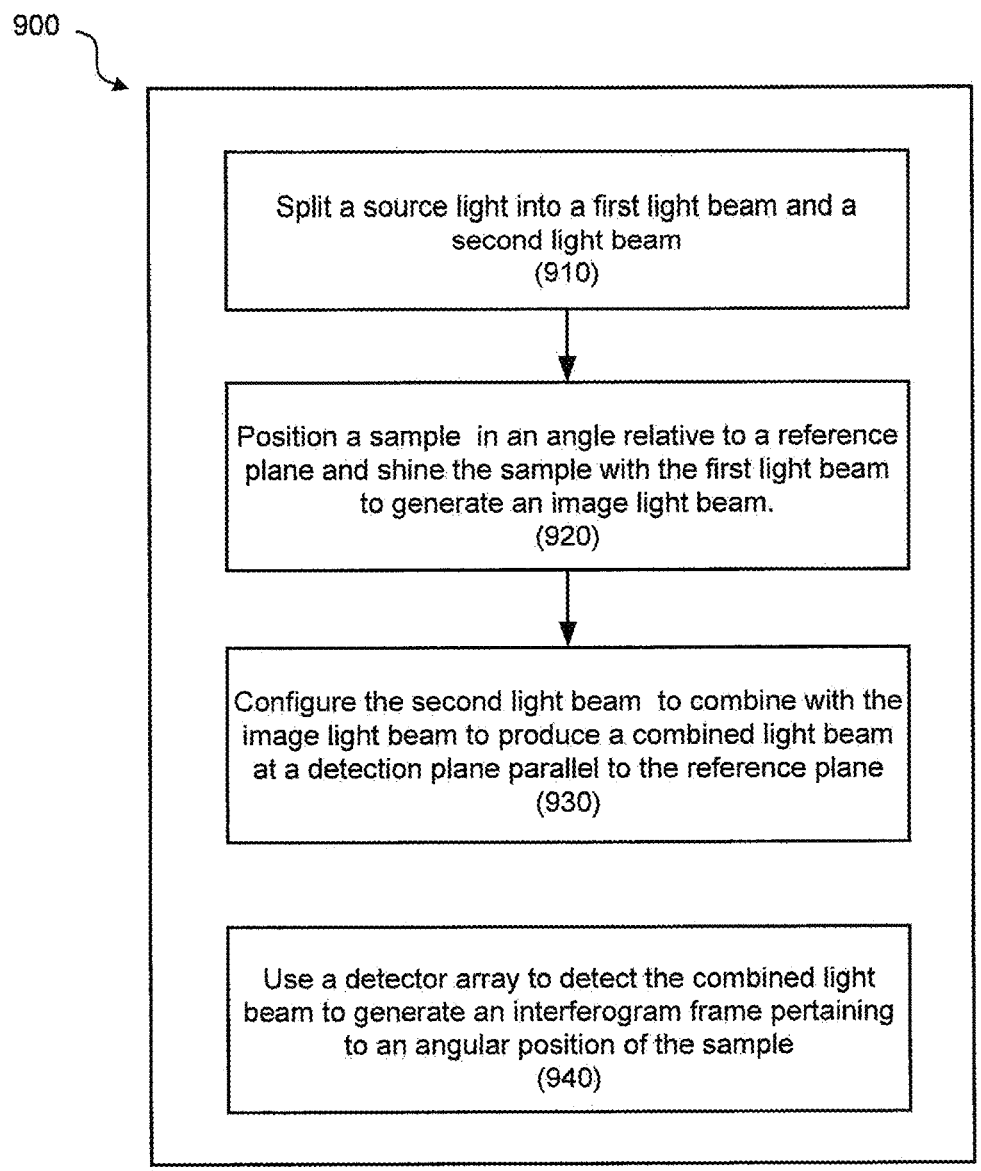
FIG. 9 is a diagram illustrating an example method for performing 3-D digital holographic refractometry, according to certain aspects of the disclosure.

FIG. 9 is a diagram illustrating an example method 900 for performing 3-D digital holographic refractometry, according to certain aspects of the disclosure. The method 900 begins with splitting (e.g., using 120 of FIG. 1) a source light into a first light beam (e.g., of waveguide 122 of FIG. 1) and a second light beam (e.g., of waveguide 124 of FIG. 1) (910). A sample (e.g., 134 of FIG. 1) positioned in an angle relative to a reference plane (e.g., XZ plane of FIG. 1) is shined with the first light beam to generate an image light beam (e.g., 140 of FIG. 1) (920). The second light beam (e.g., 150 of FIG. 1) is configured to combine with the image light beam to produce a combined light beam at a detection plane (e.g., of 160 of FIG. 1) parallel to the reference plane (930). A detector array (e.g., 160 of FIG. 1) is used to detect the combined light beam to generate an interferogram frame pertaining to an angular position of the sample (940).

Figure 10:
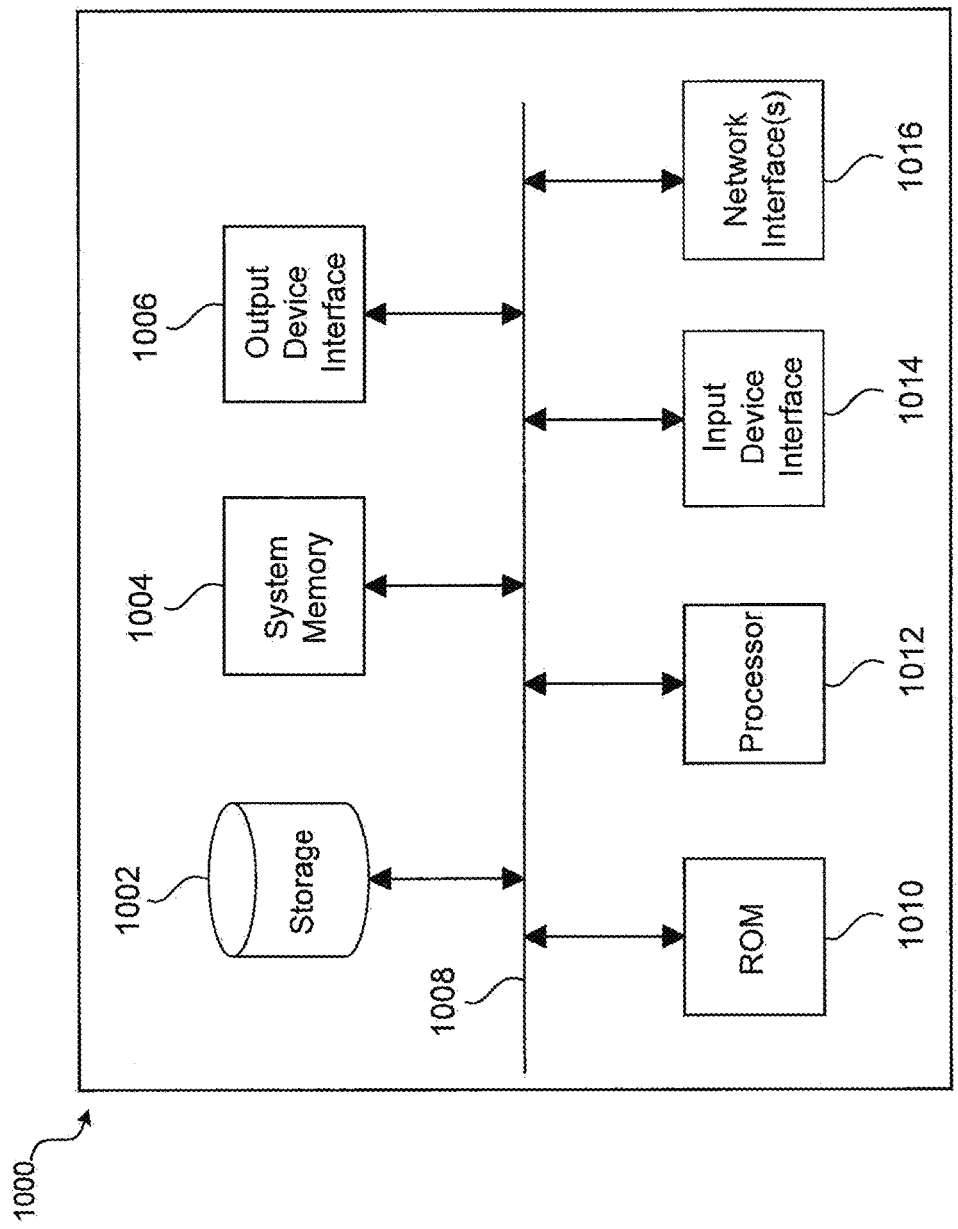
FIG. 10 is a block diagram conceptually illustrating an electronic system 500 with which aspects of the subject technology are implemented.

FIG. 10 is a block diagram conceptually illustrating an electronic system 1000 with which aspects of the subject technology are implemented. The electronic system 1000, for example, can be a network device, a media converter, a desktop computer, a laptop computer, a tablet computer, a server, a switch, a router, a base station, a receiver, a phone, or generally any electronic device that transmits signals over a network. Such an electronic system 1000 includes various types of computer readable media and interfaces for various other types of computer readable media. In one or more implementations, the electronic system 1000 can be, and/or can be a part of the system 200 of FIG. 2. The electronic system 1000 includes a bus 1008, one or more processing unit(s) 1012, a system memory 1004, a read-only memory (ROM) 1010, a permanent storage device 1002, an input device interface 1014, an output device interface 1006, and a network interface 1016, or subsets and variations thereof.

The bus 1008 collectively represents all system, peripheral, and chipset buses that communicatively connect the numerous internal devices of the electronic system 1000. In one or more implementations, the bus 1008 communicatively connects the one or more processing unit(s) 1012 with the ROM 1010, the system memory 1004, and the permanent storage device 1002. From these various memory units, the one or more processing unit(s) 1012 retrieves instructions to execute and data to process in order to execute the processes of the subject disclosure. The one or more processing unit(s) 1012 can be a single processor or a multi-core processor in different implementations. In some implementations, the one or more processing unit(s) 1012 may perform the functionalities of the modules of the system 200 of the subject technology to process interferogram frames 202 of FIG. 2 produced by the detector array 160 of FIG. 1.

The ROM 1010 stores static data and instructions that are needed by the one or more processing unit(s) 1012 and other modules of the electronic system. The permanent storage device 1002, on the other hand, is a read-and-write memory device. The permanent storage device 1002 is a non-volatile memory unit that stores instructions and data even when the electronic system 1000 is off. One or more implementations of the subject disclosure use a mass storage device (such as a magnetic or optical disk and its corresponding disk drive) as the permanent storage device 1002.

Other implementations use a removable storage device (such as a floppy disk, flash drive, and its corresponding disk drive) as the permanent storage device 1002. Like the permanent storage device 1002, the system memory 1004 is a read-and-write memory device. However, unlike the permanent storage device 1002, the system memory 1004 is a volatile read-and-write memory, such as random access memory. System memory 1004 stores any of the instructions and data that the one or more processing unit(s) 1012 needs at runtime. In one or more implementations, the processes of the subject disclosure are stored in the system memory 1004, the permanent storage device 1002, and/or the ROM 1010. From these various memory units, the one or more processing unit(s) 1012 retrieves instructions to execute and data to process in order to execute the processes of one or more implementations.

The bus 1008 also connects to the input device interface 1014 and the output device interface 1006. The input device interface 1014 enables a user to communicate information and select commands to the electronic system. Input devices used with the input device interface 1014 include, for example, alphanumeric keyboards and pointing devices (also called "cursor control devices"). The output device interface 1006 enables, for example, the display of images generated by the electronic system 1000. Output devices used with the output device interface 1006 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to the user can be any form of sensory feedback, such as visual feedback, auditory feedback, or tactile feedback; and input from the user can be received in any form, including acoustic, speech, or tactile input.

Finally, as shown in FIG. 10, the bus 1008 also couples the electronic system 1000 to one or more networks (not shown) through one or more network interfaces 1016. In this manner, the computer can be a part of one or more network of computers, such as a peer-to-peer network, a local area network ("LAN"), a wide area network ("WAN"), or an Intranet, or a network of networks, such as the Internet. Any or all components of the electronic system 1000 can be used in conjunction with the subject disclosure.

Implementations within the scope of the present disclosure can be partially or entirely realized using a tangible computer-readable storage medium (or multiple tangible computer-readable storage media of one or more types) encoding one or more instructions. The tangible computer-readable storage medium also can be non-transitory in nature.

The computer-readable storage medium can be any storage medium that can be read, written, or otherwise accessed by a general purpose or special purpose computing device, including any processing electronics and/or processing circuitry capable of executing instructions. For example, without limitation, the computer-readable medium can include any volatile semiconductor memory, such as RAM, DRAM, SRAM, T-RAM, Z-RAM, and TTRAM. The computer-readable medium also can include any non-volatile semiconductor memory, such as ROM, PROM, EPROM, EEPROM, NVRAM, flash, nvSRAM, FeRAM, eTRAM, MRAM, PRAM, CBRAM, SONOS, RRAM, NRAM, racetrack memory, FJG, and Millipede memory.

Further, the computer-readable storage medium can include any non-semiconductor memory, such as optical disk storage, magnetic disk storage, magnetic tape, other magnetic storage devices, or any other medium capable of storing one or more instructions. In some implementations, the tangible computer-readable storage medium can be directly coupled to a computing device, while in other implementations, the tangible computer-readable storage medium can be indirectly coupled to a computing device, e.g., via one or more wired connections, one or more wireless connections, or any combination thereof.

Instructions can be directly executable or can be used to develop executable instructions. For example, instructions can be realized as executable or non-executable machine code or as instructions in a high-level language that can be compiled to produce executable or non-executable machine code. Further, instructions also can be realized as or can include data. Computer-executable instructions also can be organized in any format, including routines, subroutines, programs, data structures, objects, modules, applications, applets, functions, etc. As recognized by those of skill in the art, details including, but not limited to, the number, structure, sequence, and organization of instructions can vary significantly without varying the underlying logic, function, processing, and output.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

In some aspects, the subject technology is related to a tomographic approach to 3-D holographic refractometry. The subject technology may be used in various markets, including for example and without limitation, advanced materials and sensors.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used in this specification and any claims of this application, the terms "base station", "receiver", "computer", "server", "processor", and "memory" all refer to electronic or other technological devices. These terms exclude people or groups of people. For the purposes of the specification, the terms "display" or "displaying" means displaying on an electronic device.

The description of the subject technology is provided to enable any person skilled in the art to practice the various aspects described herein. While the subject technology has been particularly described with reference to the various figures and aspects, it should be understood that these are for illustration purposes only and should not be taken as limiting the scope of the subject technology.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various aspects described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the invention has been described with reference to the disclosed aspects, one having ordinary skill in the art will readily appreciate that these aspects are only illustrative of the invention. It should be understood that various modifications can be made without departing from the spirit of the invention. The particular aspects disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative aspects disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and operations. All numbers and ranges disclosed above can vary by some amount. Whenever a numerical range with a lower limit and an upper limit is disclosed, any number and any subrange falling within the broader range are specifically disclosed. Also, the terms in the claims have their plain, ordinary meaning unless otherwise explicitly and clearly defined by the patentee. If there is any conflict in the usages of a word or term in this specification and one or more patent or other documents that may be incorporated herein by reference, the definitions that are consistent with this specification should be adopted.

What is claimed is:

1. A system for performing 3-dimensional (3-D) digital holographic refractometry, the system comprising:
   a splitter configured to split a source light into a first light beam and a second light beam;
   a tomographic optical setup configured to shine a sample with the first light beam and to generate an image light beam;
   a detector array configured to generate an interferogram signal in response to being simultaneously exposed to the image light beam and the second light beam; and
   a processor configured to generate a masked sinogram phase from the interferogram signal generated by the detector array and to perform phase error correction on the masked sinogram phase by using a phase error estimation algorithm.

2. The system of claim 1, wherein the tomographic optical setup comprises a rotation stage that is configured to rotate the sample in a plurality of angular steps.

3. The system of claim 2, wherein the tomographic optical setup is further configured to rotate the sample along more than one rotation axis.

4. The system of claim 2, wherein the detector array is configured to generate at least one interferogram signal for each position of the sample including an initial position and positions corresponding to each angular step of the plurality of angular steps.

5. The system of claim 1, wherein the detector array is positioned at an image plane or a first plane, wherein at the first plane the detector array is not saturated.

6. The system of claim 1, wherein the processor is configured to process interferogram signals generated by the detector array and to generate a 3-D refractive index profile of the sample.

7. The system of claim 6, wherein the processor is configured to perform a hologram processing for each angular position of the sample by using phase projections and performing a calibration.

8. The system of claim 7, wherein the calibration is performed by phase subtraction using a calibration phase that enables correction for lens aberration and system defocus.

9. The system of claim 7, wherein the processor is configured to perform rotation axis centering to center a sinogram relative to an axis of rotation of the sample and to unwrap a sinogram phase.

10. The system of claim 7, wherein the processor is configured to perform a radon transform iterative constraint to estimate missing information, and wherein the missing information includes information missed due to limited angular range through the sample.

11. A method for performing 3-dimensional (3-D) digital holographic refractometry, the method comprising:
    splitting a source light into a first light beam and a second light beam;
    shining a sample positioned in an angle relative to a reference plane with the first light beam to generate an image light beam;
    configuring the second light beam to combine with the image light beam to produce a combined light beam at a detection plane;
    detecting, using a detector array, the combined light beam to generate an interferogram frame pertaining to an angular position of the sample; and
    generating a masked sinogram phase from the interferogram frame generated based on the combined light beam detected by the detector array and performing phase error correction on the masked sinogram phase by using a phase error estimation algorithm.

12. The method of claim 11, further comprising using a rotation stage to rotate the sample in a plurality of angular steps and along more than one rotation axes, and wherein the more than one rotation axes comprise rotation axes at least one of which is at an angle with respect to the reference plane.

13. The method of claim 11, further comprising processing interferogram frames generated by the detector array as the angular position of the sample is varied and generating a 3-D refractive index profile of the sample.

14. The method of claim 13, wherein processing the interferogram frames comprises computing phase projections by using 2D fast Fourier transform (FFT) and performing a calibration, wherein performing the calibration comprises performing a phase subtraction using a calibration phase that enables correction for lens aberration and system defocus.

15. The method of claim 13, wherein processing the interferogram frames further comprises generating the masked sinogram phase based on intensity projections and performing phase error correction on the masked sinogram phase by using a phase error estimating algorithm.

16. The method of claim 13, wherein processing the interferogram frames further comprises performing rotation axis centering to center a sinogram relative to an axis of rotation of the sample and unwrapping a sinogram phase.

17. The method of claim 13, wherein processing the interferogram frames further comprises performing a radon transform iterative constraint to estimate missing information, and wherein the missing information includes information missed due to limited angular range through the sample.

18. A 3-dimensional (3-D) digital holographic refractometry system, the system comprising:
    a light source configured to generate a light beam;
    a splitter configured to split the light beam into a first beam and a second beam;
    an optical setup configured to hold a sample in a plurality of angular positions and to allow the sample to be shined at an angular position of the plurality of angular positions with the first beam and to generate a corresponding image light beam for the angular position of the plurality of angular positions;
    a detector array configured to generate interferogram frames in response to being simultaneously exposed to the corresponding image light beam and the second beam when the sample is held in the plurality of angular positions; and
    a processor configured to:
        process the interferogram frames to generate a 3-D refractive index profile of the sample; and
        generate a masked sinogram phase from the interferogram frames generated by the detector array and to perform phase error correction on the masked sinogram phase by using a phase error estimation algorithm.

19. The system of claim 18, wherein the optical setup comprises a writing beam configured to enable writing a refractive index onto the sample at different focal spot locations in 3D throughout the sample to achieve a desired 3-D refractive index profile.

* * * * *